United States Patent
Miao et al.

(10) Patent No.: US 7,368,242 B2
(45) Date of Patent: May 6, 2008

(54) METHOD AND KITS FOR MULTIPLEX HYBRIDIZATION ASSAYS

(75) Inventors: Xin Miao, Menlo Park, CA (US); James Ireland, San Francisco, CA (US); Paul Hardenbol, San Francisco, CA (US); Thomas Matthew Daly, Indianapolis, IN (US); Dong-Jing Fu, Carmel, IN (US); Richard D. Hockett, Fishers, IN (US)

(73) Assignee: Affymetrix, Inc., Santa Clara, CA (US)

( * ) Notice: Subject to any disclaimer, the term of this patent is extended or adjusted under 35 U.S.C. 154(b) by 146 days.

(21) Appl. No.: 11/152,460

(22) Filed: Jun. 14, 2005

(65) Prior Publication Data

US 2006/0281098 A1   Dec. 14, 2006

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3

(58) Field of Classification Search .............. 435/6; 536/23.1, 24.3
See application file for complete search history.

(56) References Cited

U.S. PATENT DOCUMENTS

| | | | | |
|---|---|---|---|---|
| 5,445,934 | A | 8/1995 | Fodor | 435/6 |
| 5,861,242 | A | 1/1999 | Chee | 435/5 |
| 5,981,174 | A | 11/1999 | Wolf | 435/6 |
| 6,355,431 | B1 | 3/2002 | Chee | 435/6 |
| 6,448,013 | B1 | 9/2002 | Arnold | 435/6 |
| 6,753,141 | B2 | 6/2004 | Bernard | 435/6 |
| 6,858,412 | B2 | 2/2005 | Willis | 435/91.1 |
| 2003/0003490 | A1 | 1/2003 | Fan | 435/6 |
| 2003/0104436 | A1 | 6/2003 | Morris | 436/6 |
| 2005/0250147 | A1* | 11/2005 | Macevicz | 435/6 |
| 2006/0019304 | A1* | 1/2006 | Hardenbol et al. | 435/6 |

OTHER PUBLICATIONS

The Stratagene Catalog p. 39 (1988).*
Shumaker et al., Mutation detection by solid phase primer extension. Human Mutation 7 : 346-354 (1996).*
Saiki et al. Analysis of enzymatically amplified -globin and HLA-DQ DNA with allele-specific oligonucleotide probes. Nature 324 : 163-166 (1986).*
Wen et al, "Rapid detection of the known SNPs of CYP2C9 using oligonucleotide microarray," World Journal of Gastroenterology, 9: 1342-1346 (2003).
Daly, "Pharmacogenetics of the major polymorphic metabolizing enzymes," Fundamental & Clinical Pharmacology, 17: 27-41 (2003).
Landi et al, "Evaluation of a microarray for genotyping polymorphisms related to xenobiotic metabolism and DNA repair," BioTechniques, 35: 816-827 (2003).
Chou et al, "Comparison of two CYP2D6 genotyping methods and assessment of genotype-phenotype relationships," Clinical Chemistry, 49: 542-551 (2003).
Linder et al, "Pharmacogenetics: a laboratory tool for optimizing therapeutic efficiency," Clinical Chemistry, 43: 254-266 (1997).
Greenspoon et al, "Validation and implementation of the PowerPlex 16 BIO system STR multiplex for forensic casework," J. Forensic Sci., 49: 71-80 (2004).
Hardenbol et al, "Multiplexed genotyping with sequence-tagged molecular inversion probes," Nature Biotechnology, 21: 673-678 (2003).
US 5,962,233, 10/1999, Livak (withdrawn)

* cited by examiner

*Primary Examiner*—Ethan Whisenant
(74) *Attorney, Agent, or Firm*—Sandra E. Wells

(57) ABSTRACT

The invention provides a method for genotyping interfering polymorphic loci in a target polynucleotide, such as a strand of genomic DNA, in a multiplex hybridization-based assay. The invention also provides nucleic acid standards for validating the performance of such hybridization-based assays. In one aspect, the method of the invention is carried out by providing for each interfering polymorphic locus one or more probes so that at least one probe is capable of forming a perfectly match duplex at the locus regardless of the characteristic sequence of an adjacent polymorphism.

4 Claims, 6 Drawing Sheets

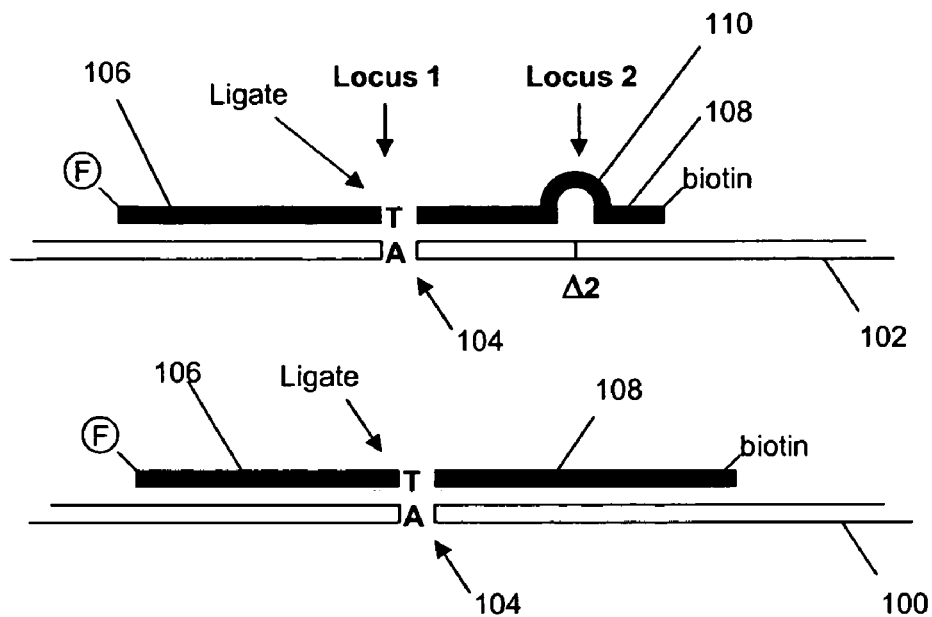
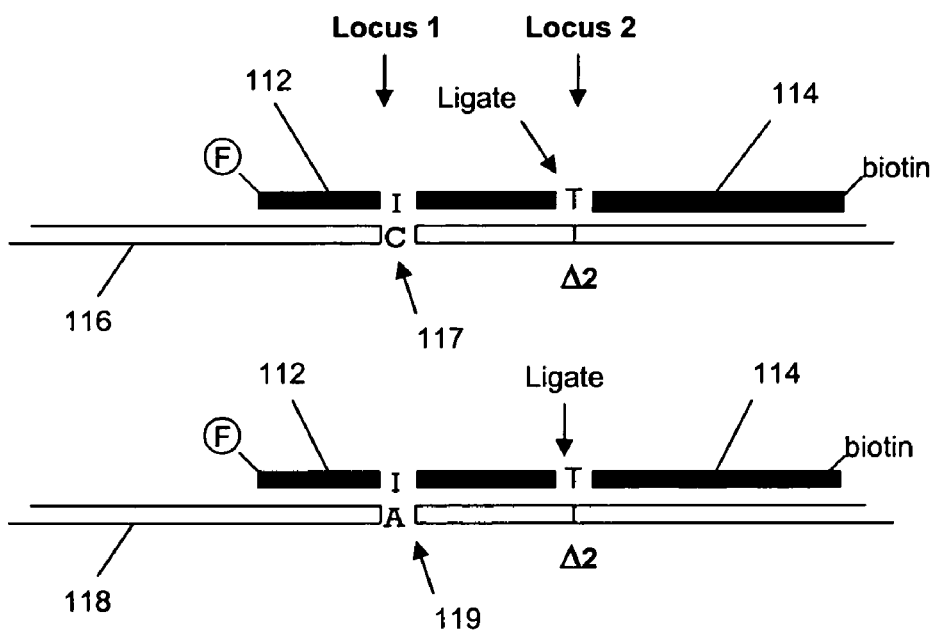
Fig. 1A
Fig. 1B

| Genotype: | Probes That Generate Signal for the Indicated Genotype | | | | | | | |
|---|---|---|---|---|---|---|---|---|
| | X Probe Signals | | | | Y Probe Signals | | | |
| (1,1) | X11 | --- | --- | --- | Y11 | --- | --- | --- |
| (1,2) | X11 | --- | X21 | --- | Y11 | Y12 | --- | --- |
| (1,3) | X11 | X12 | --- | --- | Y11 | --- | Y21 | --- |
| (1,4) | X11 | --- | --- | X22 | Y11 | --- | --- | Y22 |
| (2,2) | --- | --- | X21 | --- | --- | Y12 | --- | --- |
| (2,3) | --- | X12 | X21 | --- | --- | Y12 | Y21 | --- |
| (2,4) | --- | --- | X21 | X22 | --- | Y12 | --- | Y22 |
| (3,3) | --- | X12 | --- | --- | --- | --- | Y21 | --- |
| (3,4) | --- | X12 | --- | X22 | --- | --- | Y21 | Y22 |
| (4,4) | --- | --- | --- | X22 | --- | --- | --- | Y22 |

Fig. 2B

METHOD AND KITS FOR MULTIPLEX HYBRIDIZATION ASSAYS

FIELD OF THE INVENTION

The present invention relates to methods and kits for multiplexed hybridization-based assays, particularly for genotyping applications.

BACKGROUND

Many high throughput approaches for analyzing genetic processes and variation make use of complex mixtures of oligonucleotides to detect, sort, or manipulate gene products and/or genomic fragments, e.g. Brenner et al, Proc. Natl. Acad. Sci., 97: 1665-1670 (2000); Church et al, Science, 240: 185-188 (1988); Chee et al, Science, 274: 610-614 (1996); Shoemaker et al, Nature Genetics, 14: 450-456 (1996); Hardenbol et al, Nature Biotechnology, 21: 673-678 (2003); Kennedy et al, Nature Biotechnology, 21: 1233-1237 (2003); and the like. Such techniques are starting to be employed to genotype individuals to determine susceptibilities to a variety of conditions, including cancer, adverse drug reactions, responsiveness to targeted therapeutics, and the like, particularly in clinical trial settings. As these complex hybridization-based techniques move out of research laboratories and into medical and diagnostic applications, there will be a critical need to ensure that readouts based on the techniques are robust and valid, e.g. Food and Drug Administration, "Class II special controls guidance document: Instrumentation for clinical multiplex test systems," Guidance for Industry and FDA Staff (Mar. 10, 2005).

When polymorphisms are closely spaced along a gene or genome, certain polymorphisms, particularly insertions or deletions, at one locus may interfere with the detection of a polymorphism at adjacent loci in hybridization-based assays because of anomalous hybridization and/or interference among probes. This situation makes it difficult to determine whether a lack of signal in a readout is due to the absence of a polymorphism, probe degradation, probe interference, or other problems, e.g. Landi et al, BioTechniques, 35: 816-827 (2003). The difficulty of such determinations is exacerbated when highly complex probes are used that comprise hundreds, or even thousands, of hybridizing components.

Such difficulties may be crucial when hybridization-based assays are used to genotype a large set of xenobiotic metabolizing genes to determine an effective dosage of a drug for a patient. Metabolism of xenobiotic substances, such as drugs, is a chemical process, by which the body structurally modifies foreign compounds to enhance their solubility and facilitate their excretion. This involves two distinct metabolic phases: enzymatic oxidation, reduction, and hydrolysis reactions, which expose or add functional groups to produce polar molecules (Phase I metabolism) and addition of endogenous compounds to the molecules to further increase polarity (Phase II metabolism). The bulk of responsibility for the Phase I reactions rests on the cytochrome P450 (CYP450) superfamily of enzymes. The CYP450 family consists of 60 to 100 different monooxygenases that catalyze the oxidative metabolism of lipophilic chemicals. These, together with several members of different families of transport proteins, play a crucial role in the disposition and elimination of a diverse array of therapeutic drugs and other xenobiotics. It is now well established that significant inter-individual variability exists in patient drug disposition and response. Much of the observed heterogeneity is thought to be due to the underlying genetic variation in the human population. Individual differences at a single nucleotide of DNA, otherwise known as single nucleotide polymorphisms (SNPs), are the most abundant source of genetic variation in humans. Many SNPs with potential for altering the activity of proteins involved in drug metabolism, such as the CYP450s have been found, e.g. Daly, Fundamental & Clinical Pharmacology, 17: 27-41 (2003). Phenotypes resulting from these genetic changes can markedly influence a drugs pharmacokinetics or change its efficacy and/or toxicity profile. Several examples exist where subjects carrying certain alleles suffer from a lack of drug efficacy, due to ultrarapid metabolism (UM) or, alternatively, adverse effects from the drug treatment due to impaired drug clearance by poor metabolism (PM). In current clinical practice, the suitability of a drug for a given individual is determined by trial and error. This practice places a significant burden on healthcare systems and costs. Having an accurate genetic profile of a patient's drug metabolizing genes would help ensure that the patient receives the most effective treatment, while avoiding inadvertent adverse drug reactions in poor metabolizers.

In view of this, it would be highly desirable to have available multiplexed hybridization-based assays that could accommodate interfering polymorphisms and methods and compositions that would allow one to factor out specific causes for signal loss or variance in such assays. Such assays would be especially useful in the field of medicine and drug development, where information such assays are being increasingly used in decisions about patients and products.

SUMMARY OF THE INVENTION

The invention provides a method for detecting multiple nucleic acid targets that occur at closely adjacent loci of the same polynucleotide, such as a strand of genomic DNA, in a multiplex hybridization-based assay. The invention also provides nucleic acid standards for validating the performance of such hybridization-based assays. In one aspect, the method of the invention is carried out by providing for each interfering polymorphic locus one or more probes so that at least one probe is capable of forming a perfectly match duplex at the locus regardless of the characteristic sequence of an adjacent polymorphism. One embodiment of such method is carried out by the following steps: (i) providing for substantially every allele of each locus of interfering polymorphic loci a probe for substantially every allele of each adjacent loci of the interfering polymorphic loci, each allele of the adjacent loci having a characteristic sequence, and each such probe being capable of forming a stable duplex with the characteristic sequence of a different allele of each such adjacent loci; (ii) hydridizing the probes to a target polynucleotide containing the interfering polymorphic loci under conditions that allow stable duplexes to form whenever a probe has a sequence complementary to a locus of the interfering polymorphic loci and a characteristic sequence of an allele of an adjacent locus of the interfering polymorphic loci; and (iii) detecting the presence of probes forming stable duplexes with the target polynucleotide to determine the genotype of the interfering polymorphic loci.

In another aspect, the invention provides kits comprising nucleic acid standards for validating the performance of hybridization-based assays in detecting genotypes at interfering polymorphic loci. In one embodiment, such kits comprise a plurality of nucleic acid standards, each nucleic acid standard comprising a double stranded nucleic acid containing characteristic sequences of polymorphisms of two or more interfering polymorphic loci. In one aspect, nucleic acid standards are capable of replication. Kits of the invention may further include probes for a hybridization-based assay, wherein such assay includes probes specific for at least one interfering polymorphic loci.

BRIEF DESCRIPTION OF THE FIGURES

FIGS. 1A-1C diagrammatically illustrate the concept of interfering polymorphic loci for two and three polymorphic loci.

FIGS. 2A-2B illustrate a pattern of signals generated by probes specific for a pair of interfering polymorphic loci.

DEFINITIONS

Figure 1C:
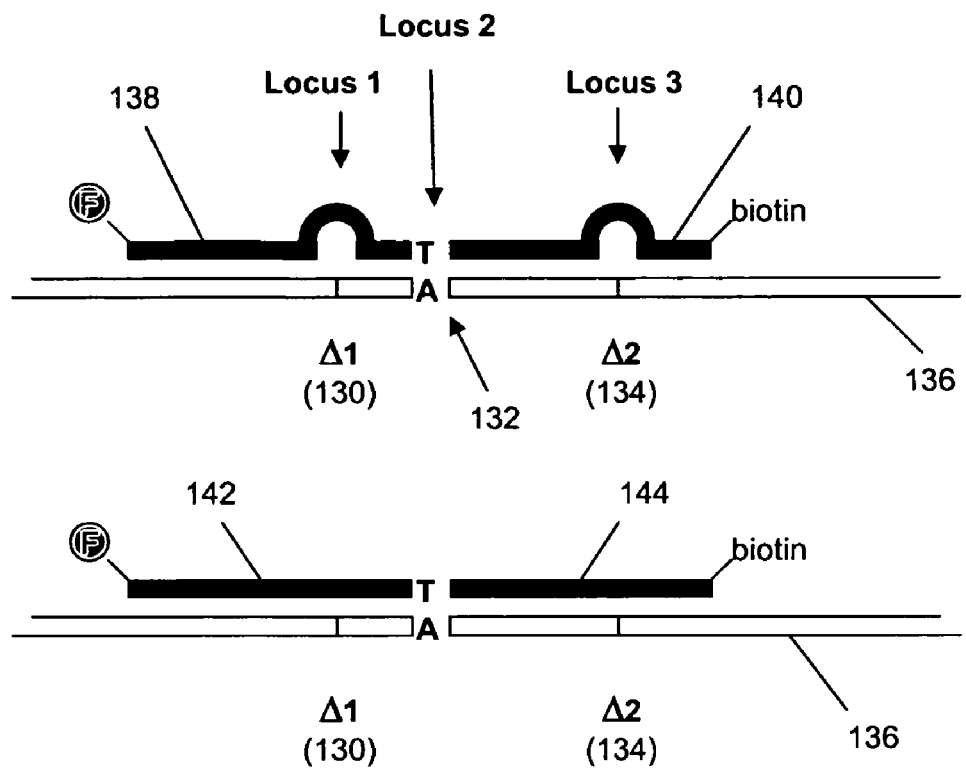

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Addressable" in reference to tag complements means that the nucleotide sequence, or perhaps other physical or chemical characteristics, of an end-attached probe, such as a tag complement, can be determined from its address, i.e. a one-to-one correspondence between the sequence or other property of the end-attached probe and a spatial location on, or characteristic of, the solid phase support to which it is attached. Preferably, an address of a tag complement is a spatial location, e.g. the planar coordinates of a particular region containing copies of the end-attached probe. However, end-attached probes may be addressed in other ways too, e.g. by microparticle size, shape, color, frequency of micro-transponder, or the like, e.g. Chandler et al, PCT publication WO 97/14028.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Complementary or substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. In one aspect, stable duplex means that a duplex structure is not destroyed by a stringent wash, e.g. conditions including tempature of about 5° C. less that the $T_m$ of a strand of the duplex and low monovalent salt concentration, e.g. less than 0.2 M, or less than 0.1 M. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Genetic locus," or "locus" in reference to a genome or target polynucleotide, means a contiguous subregion or segment of the genome or target polynucleotide. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In one aspect, a genetic locus refers to any portion of genomic sequence, including mitochondrial DNA, from a single nucleotide to a segment of few hundred nucleotides, e.g. 100-300, in length. Usually, a particular genetic locus may be identified by its nucleotide sequence, or the nucleotide sequence, or sequences, of one or both adjacent or flanking regions.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1M, more usually less than about 500 mM and less than about 200 mM. Hybridization temperatures can be as low as 5° C., but are typically greater than 22° C., more typically greater than about 30° C., and preferably in excess of about 37° C. Hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook, Fritsche and Maniatis. "Molecular Cloning A laboratory Manual" $2^{nd}$ Ed. Cold Spring Harbor Press (1989) and Anderson "Nucleic Acid Hybridization" $1^{st}$ Ed., BIOS Scientific Publishers Limited (1999), which are hereby incorporated by reference in its entirety for all purposes above. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Hybridization-based assay" means any assay that relies on the formation of a stable duplex or triplex between a probe and a target nucleotide sequence for detecting or measuring such a sequence. In one aspect, probes of such assays anneal to (or form duplexes with) regions of target sequences in the range of from 8 to 100 nucleotides; or in other aspects, they anneal to target sequences in the range of from 8 to 40 nucleotides, or more usually, in the range of from 8 to 20 nucleotides. A "probe" in reference to a hybridization-based assay mean a polynucleotide that has a sequence that is capable of forming a stable hybrid (or triplex) with its complement in a target nucleic acid and that is capable of being detected, either directly or indirectly. Hybridization-based assays include, without limitation, assays based on use of oligonucleotides, such as polymerase chain reactions, NASBA reactions, oligonucleotide ligation reactions, single-base extensions of primers, circularizable probe reactions, allele-specific oligonucleotides hybridizations, either in solution phase or bound to solid phase supports, such as microarrays or microbeads. There is extensive guidance in the literature on hybridization-based assays, e.g. Hames et al, editors, Nucleic Acid Hybridization a Practical Approach (IRL Press, Oxford, 1985); Tijssen, Hybridization with Nucleic Acid Probes, Parts I & II (Elsevier Publishing Company, 1993); Hardiman, Microarray Methods and Applications (DNA Press, 2003); Schena, editor, DNA Microarrays a Practical Approach (IRL Press, Oxford, 1999); and the like. In one aspect, hybridization-based assays are solution phase assays; that is, both probes and target sequences hybridize under conditions that are substantially free of surface effects or influences on reaction rate. A solution phase assay may include circumstance where either probes or target sequences are attached to microbeads.

"Interfering polymorphic loci" mean closely spaced loci having sequence variants, or alleles, usually insertions, detections, or substitutions, that are sought to be determined by a hybridization-based assay. In one aspect, interfering polymorphic loci are a pair of closely spaced loci in which at least one locus of the pair contains two or more alternative forms, each having a characteristic sequence, such that the presence of at least one characteristic sequence destabilizes a probe specific for the other locus of the pair on the same DNA strand. Characteristic sequences of alleles may be identified in conventional databases, e.g. dbSNP, or the like. The region of a target polynucleotide or genome that interfering polymorphic loci span depends in part on the nature of the probes employed in a hybridization-based assay. Thus, in one aspect, members of a pair of interfering polymorphic loci are within 40 nucleotides of one another; or in another aspect such members may be within 20 nucleotides of one another.

"Kit" refers to any delivery system for delivering materials or reagents for carrying out a method of the invention. In the context of assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials for assays of the invention. In one aspect, kits of the invention comprise probes specific for interfering polymorphic loci. In another aspect, kits comprise nucleic acid standards for validating the performance of probes specific for interfering polymorphic loci. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476,930; Fung et al, U.S. Pat. No. 5,593,826; Kool, U.S.

Pat. No. 5,426,180; Landegren et al, U.S. Pat. No. 5,871, 921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213.

"Microarray" refers to a solid phase support having a planar surface, which carries an array of nucleic acids, each member of the array comprising identical copies of an oligonucleotide or polynucleotide immobilized to a spatially defined region or site, which does not overlap with those of other members of the array; that is, the regions or sites are spatially discrete. Spatially defined hybridization sites may additionally be "addressable" in that its location and the identity of its immobilized oligonucleotide are known or predetermined, for example, prior to its use. Typically, the oligonucleotides or polynucleotides are single stranded and are covalently attached to the solid phase support, usually by a 5'-end or a 3'-end. The density of non-overlapping regions containing nucleic acids in a microarray is typically greater than 100 per $cm^2$, and more preferably, greater than 1000 per $cm^2$. Microarray technology is reviewed in the following references: Schena, Editor, Microarrays: A Practical Approach (IRL Press, Oxford, 2000); Southern, Current Opin. Chem. Biol., 2: 404-410 (1998); Nature Genetics Supplement, 21: 1-60 (1999). As used herein, "random microarray" refers to a microarray whose spatially discrete regions of oligonucleotides or polynucleotides are not spatially addressed. That is, the identity of the attached oligonucleoties or polynucleotides is not discernable, at least initially, from its location. In one aspect, random microarrays are planar arrays of microbeads wherein each microbead has attached a single kind of hybridization tag complement, such as from a minimally cross-hybridizing set of oligonucleotides. Arrays of microbeads may be formed in a variety of ways, e.g. Brenner et al, Nature Biotechnology, 18: 630-634 (2000); Tulley et al, U.S. Pat. No. 6,133,043; Stuelpnagel et al, U.S. Pat. No. 6,396,995; Chee et al, U.S. Pat. No. 6,544,732; and the like. Likewise, after formation, microbeads, or oligonucleotides thereof, in a random array may be identified in a variety of ways, including by optical labels, e.g. fluorescent dye ratios or quantum dots, shape, sequence analysis, or the like.

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structural Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999)(two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, β$_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polymorphism" or "genetic variant" means a substitution, inversion, insertion, or deletion of one or more nucleotides at a genetic locus, or a translocation of DNA from one genetic locus to another genetic locus. In one aspect, polymorphism means one of multiple alternative nucleotide sequences that may be present at a genetic locus of an individual and that may comprise a nucleotide substitution, insertion, or deletion with respect to other sequences at the same locus in the same individual, or other individuals within a population. An individual may be homozygous or heterozygous at a genetic locus; that is, an individual may have the same nucleotide sequence in both alleles, or have a different nucleotide sequence in each allele, respectively. In one aspect, insertions or deletions at a genetic locus comprises the addition or the absence of from 1 to 10 nucleotides at such locus, in comparison with the same locus in another individual of a population (or another allele in the same individual). Usually, insertions or deletions are with respect to a major allele at a locus within a population, e.g. an allele present in a population at a frequency of fifty percent or greater.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moities, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 14 to 36 nucleotides.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak non-covalent chemical interactions, such as Van der Waal forces, hydrogen bonding, base-stacking interactions, ionic and hydrophobic interactions, and the like, dominate the interaction of the molecules.

"$T_m$" is used in reference to "melting temperature." Melting temperature is the temperature at which a population of double-stranded nucleic acid molecules becomes half dissociated into single strands. Several equations for calculating the Tm of nucleic acids are well known in the art. As indicated by standard references, a simple estimate of the Tm value may be calculated by the equation. Tm=81.5+0.41 (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of Tm.

"Sample" means a quantity of material from a biological, environmental, medical, or patient source in which detection or measurement of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

DETAILED DESCRIPTION OF THE INVENTION

In one aspect, the invention provides a method and kits for performing hybridization-based assays that determine genotypes and/or haplotypes at one or more interfering polymorphic loci. In one aspect of the method of the invention, for each allele of each locus of a pair of interfering polymorphic loci probes are provided that form perfectly matched duplexes with each allele of the other locus. In this manner, at least one probe will be available to form a proper hybrid for detecting each haplotype of the interfering polymorphic loci. Such probes are then combined under hybridization conditions with a sample containing target polynucleotides containing interfering polymorphic loci in accordance with the hybridization-based assay in which they are employed.

In another aspect, the invention provides compositions and associated kits for validating the performance of hybridization-based assays containing probes specific for interfering polymorphic loci. Compositions of the invention comprise, either separately or as one or more mixtures, nucleic acid standards, or reference sequences, that contain the sequences of interfering polymorphic loci, which a corresponding a hybridization-based assay is designed to detect. When a hybridization-based assay is employed to genotype individuals, e.g. patients being considered for chemotherapy, assay results may be validated by application of the assay to the nucleic acid standards. This aspect of the invention is particularly useful for highly multiplexed hybridization-based assays that are capable of identifying genotypes at many tens of loci to many thousands of loci in the same assay reaction, where a subset of the loci may be interfering polymorphic loci. In both of the above aspects, probes or standards for interfering polymorphic loci may be present with probes or standards for non-interfering polymorphic loci, respectively. In one aspect, nucleic acid standards are provided for each haplotype of each interfering polymorphic loci being analyzed by a hybridization-based assay. In another aspect, nucleic acid standards may be provided for a subset of possible haplotypes of interfering polymorphic loci.

A pair of interfering polymorphic loci is illustrated in FIGS. 1A and 1B for the case where there are two alternative alleles at each locus. At locus 1 a single allele, i.e. an A:T basepair, is shown. Locus 2 is biallelic for a first sequence (100) and a deletion variation of it (102) (indicated by the symbol "$\Delta_2$"). FIGS. 1A and 1B also show probes from a hybridization-based assay (in this case, components of a oligonucleotide ligation assay are represented, e.g. as described in Whiteley et al, U.S. Pat. No. 4,883,750). At locus 1, the target nucleic acid (100 or 102) has an "A" (104), and at locus 2, the target nucleic acid is present in two variations: sequence (100) or sequence (102) that contains a deletion within the site at which probe (108) hybridizes. Thus, if only probes (106) and (108) were used in the assay, the deletion variant (102) would completely preclude probe (108) from annealing, or at best, would severely destabilize any duplex formed by formation of loop (110), or by the formation of other unstable structures. In accordance with one aspect of the invention, whenever such an interfering polymorphic locus occurs, a separate probe is provided for each sequence variant at that locus. Thus, in the system of FIG. 1A, an additional pair of probes would be provided, one of which would form a perfectly matched duplex with the deletion sequence variant (102) at locus 2.

As illustrated in FIG. 1B, in one aspect of the invention, where one locus in a pair of interfering polymorphic loci consists of a single base substitution, a universal nucleotide may be used in a probe specific for a polymorphism in an adjacent interfering polymorphic locus. Thus, a single pair of probes (112) and (114) specific for the deletion polymorphism at locus 2 may be used even though there are two substitution variants, "C" (117) and "A" (119), in the hybridization site of probe (112). In this illustration, deoxyinosine is used in probe (112) since it may basepair with either A or C. Other such universal bases, or corresponding universal nucleotides, may be employed, e.g. 5-nitroindole, 4-nitroindole, and the like. The following references, which are incorporated by reference, provide guidance for selection of universal bases, or nucleosides, for incorporation into hybridization probes: U.S. Pat. Nos. 6,313,286 and 6,239,159; The Glen Report, 8: 1-5 (Glen Research, Sterling, Va., 1995); Loakes, Nucleic Acids Research, 29: 2437-2447 (2001); Ball et al, Nucleic Acids Research, 26: 5225-5227 (1998); Loakes et al, J. Mol. Biol., 270: 426-435 (1997). As used herein, the term "universal base" refers to a natural or unnatural base or base analog of a nucleoside (or nucleoside analog, as the case may be) that has the property of being able to form Watson-Crick basepairs with two or more natural nucleosides.

As illustrated in FIG. 1C, interfering polymorphic loci may include three adjacent polymorphic loci, which in FIG. 1C comprise a deletion $\Delta_1$ (130), a base substitution (132), and a deletion $\Delta_2$ (134). In the top diagram of FIG. 1C, probes (138) and (140) specific for locus 2 are disrupted by the deletion polymorphisms at locus 1 and locus 3. In the bottom diagram, the correct-sequence probes, (142) and (144), for the two deletions are shown. In general, for each polymorphism at locus 2, there are as many as four alternative probes: ($\Delta_1$ present, $\Delta_2$ present), ($\Delta_1$ present, $\Delta_2$ absent), ($\Delta_1$ absent, $\Delta_2$ present), ($\Delta_1$ absent, $\Delta_2$ absent).

Figure 2A:
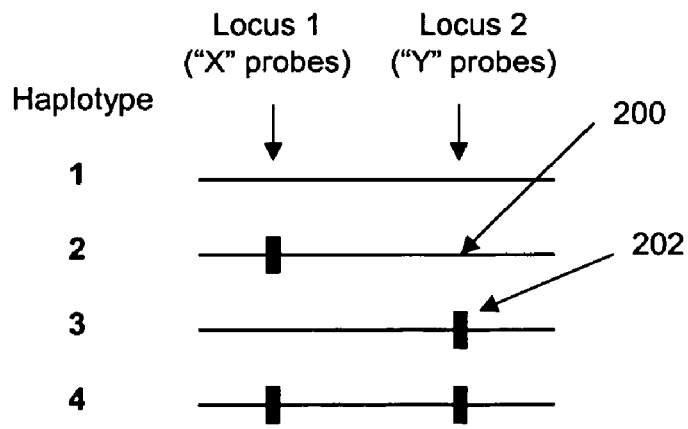

In FIGS. 2A and 2B, all possible genotypes and signal generating probes are illustrated for a pair of interfering polymorphic loci, where each locus has two possible alleles (shown by the absence of a bar (200) or as a bar (202)). Occasionally, these will be referred to as the "major" allele and "minor" allele, respectively, for convenience. In this illustration, the alleles are shown as if they occur in an independent manner. However, in practice, such closely spaced alleles only very rarely would be independent. Typically, only three genotypes are observed in a population at such a pair of interfering polymorphic loci, e.g. 1, 2, and 3, of FIG. 2A. Thus, in some aspects of the invention, nucleic acid standards and/or probes may be provided only for a subset of genotypes, e.g. 1, 2, and 3, of FIG. 2A. As used herein, "substantially every" in reference to genotypes at interfering polymorphic loci means that in particular embodiments nucleic acid standard and/or probes corresponding to very rare genotypes are not included in a set or mixture. As used herein, "very rare" in reference to genotypes means less than 0.1% of a or less than 0.01% of a population, Nonetheless, for the sake of illustration, all theoretically possible genotypes are illustrated in FIG. 2B together with probes that would generate signals in an assay where the indicated genotype is present.

Probes of the invention are combined under appropriate hybridization conditions with a sample to be genotyped or with a set of nucleic acid standards for validation of an assay. Such conditions depend on the hybridization-based assay being employed, for which there is significant guidance available to one of ordinary skill, as noted below. For example, in one aspect, molecular inversion probes are provided for detecting interfering polymorphic loci using procedures and conditions as set forth below.

Genetic Systems

As mentioned above, methods and compositions of the invention are particularly applicable to systems of polymorphic genes that are responsible for or involve in a phenotypic response or characteristic. Examples of such systems include xenobiotic metabolizing genes, HLA genes, tumor suppressor genes, cell cycle control genes, oncogenes, and the like. Of particular interest are genes responsible for metabolizing drugs and other xenobiotic substances, e.g. as described in Linder et al, Clin. Chem., 43: 254-266 (1997); Landi et al (cited above); Daly, Fundamental & Clinical Pharmacology, 17: 27-41 (2003); and the like. In one aspect, the invention includes hybridization-based assays to determine the genotype of a plurality of loci in genes of xenobiotic metabolizing enzymes selected from the tables below. (Below conventional gene nomenclature is used. Nucleic acid sequences and other information for the indicated genes may be obtained in various public databases, such as dbSNP (http://www.ncbi.nlm.nih.gov/SNP/), HUGO Gene Nomenclature Committee website (http://www.gene.ucl.ac.uk/nomenclature/index.html); ENSEMBL (http://www.ensembl.org), and the like.

TABLE I

Exemplary Xenobiotic Metabolizing Genes

| | | | |
|---|---|---|---|
| ABCB1 | CYP2E1 | GSTP1 | SLC22A2 |
| ABCC2 | CYP2J2 | NAT1 | TPMT |
| CDA | CYP3A4 | NAT2 | UGT1A1 |
| CYP1A2 | CYP3A5 | CYP2C8 | |
| CYP2A6 | DPYD | CYP2C9 | |
| CYP2B6 | FMO2 | SLC15A2 | |
| CYP2C19 | FMO3 | SLC21A6 | |
| CYP2D6 | GSTM1 | SLC22A1 | |

The following pairs of polymorphisms of genes in the above table are interfering polymorphic loci for hybridization-based assays in which pairs of oligonucleotides having lengths in the range of from 16 to 24 nucleotides are ligated for polymorphism detection:

TABLE II

Exemplary Interfering Polymorphic Loci in Xenobiotic Metabolizing Genes

| Gene | Locus 1 | Locus 2 | Locus 3 |
|---|---|---|---|
| ABCB1 | rs1045642 | rs17149694 | |
| ABCB1 | MDR1*14A61G | rs9332385 | |
| ABCC2 | rs717620 | rs8187711 | |
| CYP1A2 | CYP1A2*1K, -740TG | CYP1A2*1K, -730CT | |
| CYP2A6 | CYP2A6*8, 6600G | CYP2A6*5 (rs5031017) | |
| CYP2A6 | CYP2A6*7, 6558TC (rs5031016) | rs6413474 | |
| CYP2B6 | CYP2B6*8 | CYP2B6*13076GA | |
| CYP2B6 | CYP2B6*4 | CYP2B6*3 | |
| CYP2C19 | CYP2C19*14, 50TC | rs17882687 | |
| CYP2C19 | CYP2C19*6, 395GA | rs17882291 | |
| CYP2C19 | CYP2C19*10, 680CT | CYP2C19*2, 681GA | |
| CYP2C19 | CYP2C19*9, 991AG | rs17878422 | |
| CYP2C8 | CYP2C8*2, 805AT | rs1058930 | |
| CYP2C9 | CYP2C9*2 | CYP2C9*8 (rs7900194) | |
| CYP2C9 | CYP2C9*10 | rs9332131 | |
| CYP2C9 | CYP2C9*3 | CYP2C9*4 | CYP2C9*5 |
| CYP2D6 | CYP2D6*42, 3259insGT | rs1058172 | |
| CYP2D6 | CYP2D6*44, 2950GC | CYP2D6*7 | |

TABLE II-continued

Exemplary Interfering Polymorphic Loci in Xenobiotic Metabolizing Genes

| Gene | Locus 1 | Locus 2 | Locus 3 |
|---|---|---|---|
| CYP2D6 | CYP2D6*38 | CYP2D6*21, 2573insC | |
| CYP2D6 | CYP2D6*3A | CYP2D6*19, 2539delAACT | |
| CYP2D6 | CYP2D6*20, 1973insG | rs3831704 | |
| CYP2D6 | CYP2D6*4, 1846GA | rs11568728 | |
| CYP2D6 | CYP2D6*17, 1023CT | rs1081003 | |
| CYP2D6 | CYP2D6*15 | CYP2D6*12, 124GA | |
| CYP2D6 | CYP2D6*42, -1584GC | rs7511593 | |
| CYP3A4 | CYP3A4*17 (rs4987161) | 3A4RS4987159 | |
| CYP3A5 | CYP3A5*3B, H30Y | CYP3A5*8 | |
| DPYD | DPYD*2A | DPYD*3 | |
| FMO3 | FMO3L360P | rs2066532 | |
| GSTM1 | GSTM1, AB | rs1056806 | |
| NAT1 | rs4987076 | rs4986990 | |
| NAT1 | rs5030809 | NAT1*14G560A | |
| NAT2 | rs1801279 | rs1805158 | |
| NAT2 | rs1799931 | NAT2, A845C | |
| SLC21A6 | rs2306283 | rs11045818 | |
| SLC21A6 | OATPCA467G | rs11045819 | |
| SLC22A1 | OCT1C88R | OCT1L85F | |
| SLC22A1 | rs2282143 | OCT1R342H | |
| SLC22A1 | OCT1G401S | OCT1I403 | |
| SLC22A2 | rs8177516 | rs8177515 | |
| SLC22A2 | rs8177507 | rs8177508 | |
| TPMT | TPMT*8 | rs1800584 | |
| TPMT | TPMT*3B | rs2842934 | |
| UGT1A1 | UGT1A1*28 | rs873478 | |
| UGT1A1 | UGT1A1*27 | UGT1A1*35 | |

Further genes of interest for determining an individuals ability to metabolize a selected xenobiotic compound include those listed in Table III.

TABLE III

Further Exemplary Xenobiotic Metabolizing Genes

| | | | |
|---|---|---|---|
| CYP1A1 | CYP1B1 | CYP2C18 | CYP3A7 |
| GSTT1 | GSTM3 | GSTA1 | UGT1A6 |
| UGT1A7 | UGT2B4 | UGT2B7 | UGT2B15 |
| ADH1B | ALDH2 | APE1 | CDKN2A |
| COMT | DRD2 | DRD4 | EPHX1 |
| ERCC1 | ERCC2 | ERCC4 | ERCC5 |
| GRPR | GSTA4 | LIG3 | MDM2 |
| MGMT | MPO | NQO1 | OGG1 |
| PCNA | POLB | SLC6A3 | SOD2 |
| TP53 | XRCC1 | XRCC2 | XRCC3 |
| XRCC9 | | | |

Hybridization-Based Assays

As mentioned above, the invention relates to the use of hybridization-based assays to detect or measure interfering polymorphic loci. Such assays are widely used in multiplexed formats to simultaneously genotype DNA samples at multiple loci, e.g. allele-specific muliplex PCR, arrayed primer extension (APEX) technology, variation detection arrays, solution phase primer extension or ligation assays, and the like, described in the following references: Shumaker et al, Hum. Mut., 7: 346-354 (1996); Cronin et al, U.S. Pat. No. 6,468,744; Huang et al, U.S. Pat. Nos. 6,709, 816 and 6,287,778; Fan et al, U.S. patent publication 2003/ 0003490; Chee et al, U.S. Pat. No. 6,355,431; Gunderson et al, U.S. patent publication 2005/0037393; Hacia et al, U.S. Pat. No. 6,342,355; Kennedy et al, Nature Biotechnology, 21: 1233-1237 (2003); Chou et al, Clin. Chem., 49: 542-551 (2003); and the like.

In one aspect, hybridization-based assays include circularizing probes, such as padlock probes, rolling circle probes, molecular inversion probes, linear amplification molecules for multiplexed PCR, and the like, e.g. padlock probes being disclosed in U.S. Pat. Nos. 5,871,921; 6,235, 472; 5,866,337; and Japanese patent JP 4-262799; rolling circle probes being disclosed in Aono et al, JP-4-262799; Lizardi, U.S. Pat. Nos. 5,854,033; 6,183,960; 6,344,239; molecular inversion probes being disclosed in Hardenbol et al (cited above) and in Willis et al, U.S. patent publication 2004/0101835; and linear amplification molecules being disclosed in Faham et al, U.S. patent publication 2003/ 0104459; all of which are incorporated herein by reference. Such probes are desirable because non-circularized probes can be digested with single stranded exonucleases thereby greatly reducing background noise due to spurious amplifications, and the like. In the case of molecular inversion probes (MIPs), padlock probes, and rolling circle probes, constructs for generating labeled target sequences are formed by circularizing a linear version of the probe in a template-driven reaction on a target polynucleotide followed by digestion of non-circularized polynucleotides in the reaction mixture, such as target polynucleotides, unligated probe, probe concatatemers, and the like, with an exonuclease, such as exonuclease I.

Figure 3:
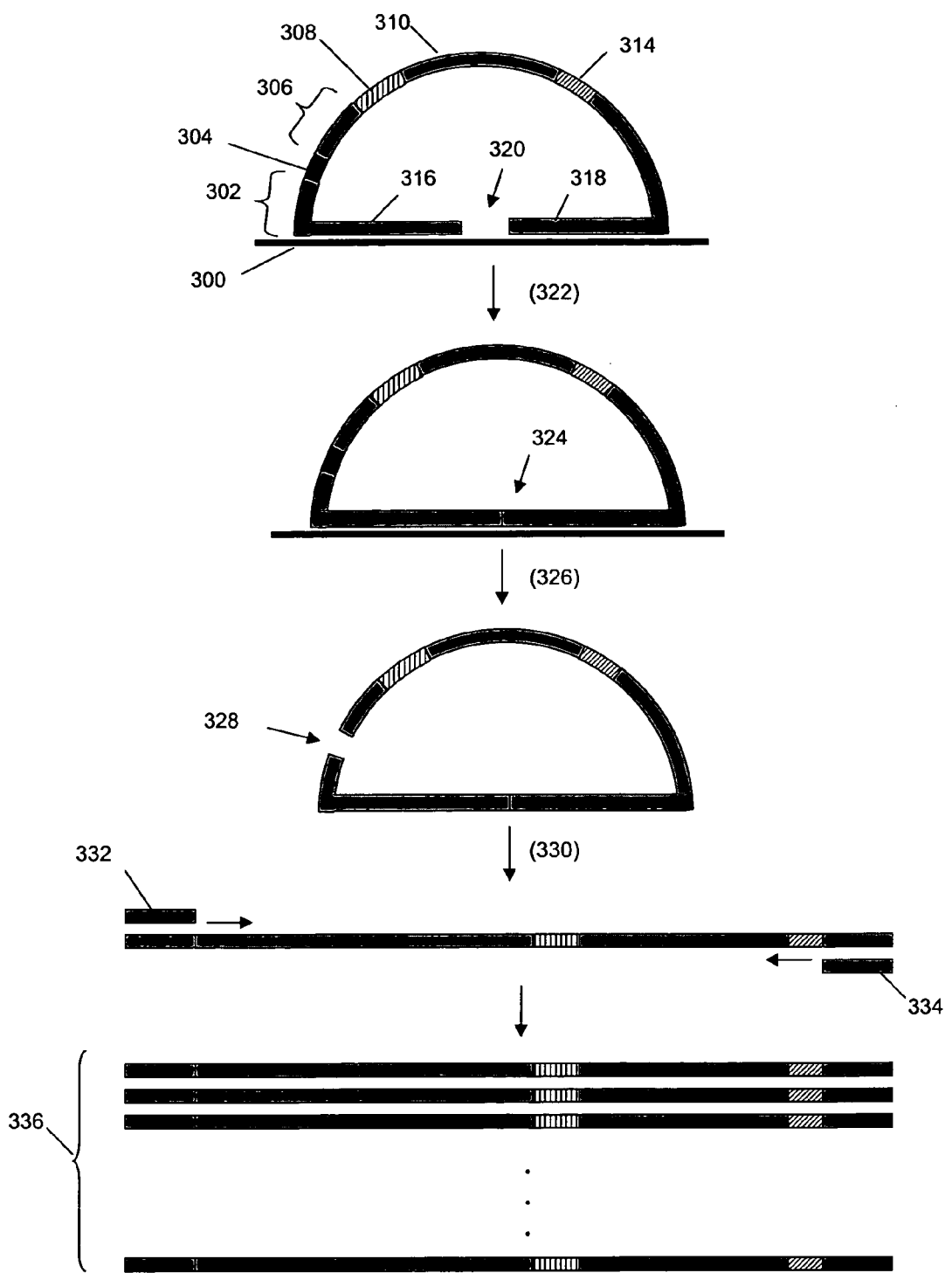
FIG. 3 illustrates a molecular inversion probe that may be used with the invention.

FIG. 3 illustrates a molecular inversion probe and how it can be used to generate an amplicon after interacting with a target polynucleotide in a sample. A linear version of the probe is combined with a sample containing target polynucleotide (300) under conditions that permit target-specific region 1 (316) and target-specific region 2 (318) to form stable duplexes with complementary regions of target polynucleotide (300). The ends of the target-specific regions may abut one another (being separated by a "nick") or there may be a gap (320) of several (e.g. 1-10 nucleotides) between them. In either case, after hybridization of the target-specific regions, the ends of the two target specific regions are covalently linked by way of a ligation reaction or an extension reaction followed by a ligation reaction, i.e. a so-called "gap-filling" reaction. The latter reaction is carried out by extending with a DNA polymerase a free 3' end of one of the target-specific regions so that the extended end abuts the end of the other target-specific region, which has a 5' phosphate, or like group, to permit ligation. In one aspect, a molecular inversion probe has a structure as illustrated in FIG. 3. Besides target-specific regions (316 and 318), in sequence such a probe may include first primer binding site (302), cleavage site (304), second primer binding site (306), first tag-adjacent sequences (308) (usually restriction endonuclease sites and/or primer binding sites) for tailoring one end of a labeled target sequence containing oligonucleotide tag (310), and second tag-adjacent sequences (314) for tailoring the other end of a labeled target sequence. Alternatively, cleavage-site (304) may be added at a later step by amplification using a primer containing such a cleavage site. In operation, after specific hybridization of the target-specific regions and their ligation (322), the reaction mixture is treated with a single stranded exonuclease that preferentially digests all single stranded nucleic acids, except circularized probes. After such treatment, circularized probes are treated (326) with a cleaving agent that cleaves the probe between primer (302) and primer (306) so that the structure is linearized (330). Cleavage site (304) and its corresponding cleaving agent is a design choice for one of ordinary skill in the art. In one aspect, cleavage site (304) is a segment containing a sequence of uracil-containing nucleotides and the cleavage agent is treatment with uracil-DNA glycosylase followed by heating. After the circularized probes are opened, the linear product is amplified, e.g. by PCR using primers (332) and (334), to form amplicons (336). A multiplexed readout may be obtained from amplicon (336) by labeling and excising oligonucleotide tag (310) and specifically hybridizing the labeled tags to a microarray of tag complements, e.g. a GenFlex array (Affymetrix, Santa Clara, Calif.); a bead array (Illumina, San Diego, Calif.); or a fluid array, e.g. Chandler et al, U.S. Pat. No. 5,981,180 (Luminex, Austin, Tex.).

In one aspect of the invention, probes may be selected for very large sets of targets in multiplexed hybridization-based assays that do not produce adequate signals for analysis because there exist multiple regions in a genome having very similar sequences, e.g. gene duplications, homologous families, and the like, Strachan and Read, Human Molecular Genetics, 3$^{rd}$ Edition (Garland Science/Taylor & Francis Group, 2003). In such cases, the subset of targets may be pre-amplified, e.g. with PCR or like method, prior to conducting a hybridization-based assay. That way, the concentration of desired sections of the genome containing the correct target regions can be increased, thereby allowing relatively more probe to bind to the correct target regions than the undesired regions. Such pre-amplifications may take place in a separate reaction, the product of which may then be combined with additional sample for application of the hybridization-based assay, or the pre-amplification may take place as a preliminary-stage reaction in the same reaction mixture as the hybridization-based assay. The parameters of such pre-amplification reaction are a matter of design choice for those skilled in the art and may involve an amount of routine experimentation. Alternatively, in some cases, probe signals may be increased by increasing the relative concentration of probe directed to loci associated with low signals, thereby promoting the formation of duplexes between selected probes and their target loci.

In accordance with the invention, the degree of multiplexing in a hybridization-based assay may vary widely. In one aspect, such assays of the invention may have a degree of multiplexing greater than 100 probes, or they may have a degree of multiplexing in a range of from 100 to 10,000 probes, or in a range of from 100 to 100,000 probes.

Nucleic Acid Standards

In one aspect, nucleic acid standards of the invention comprise one or more double stranded DNAs that contain sequences identical to those of the interfering polymorphic loci that are to be detected or measured in a hybridization-based assay. As mentioned above, the purpose of the standards is to validate that a hybridization-based assay is making correct determinations of the target sequences it is designed to detect or quantify. Such validation includes confirmation that correct determinations are being made of (i) the genotypes of specific interfering polymorphic loci, and (ii) the presence or absence of heterozygote and homozygote genotypes. Standards may also be used to develop new multiplexed hybridization-based assays by providing targets on which to test new component probes. A set of nucleic acid tandards of the invention may be provided such that there is one standard for each target loci, or a set of nucleic acid standards may be larger or smaller than the number of loci being analyzed in a particular hybridization-based assay. For example, a single set of nucleic acid standards may be employed with a family of different hybridization-based assays where, for example, each assay may be directed to a different subset of loci and the nucleic acid standard may contain sequences for all the different subsets. Usually, nucleic acid standards are provided in kits that may come together with, or separately from, probes for a hybridization-base assay. In one aspect, a kit of nucleic acid standards comprises one or more double stranded DNAs each containing a sequence of a pair or triplet of interfering polymorphic loci. In another aspect, such a kit contains at least one double stranded DNA containing a sequence of every interfering polymorphic loci, including a separate sequence for each haplotype at each such loci, being analyzed by a particular hybridization-based assay. In some embodiments, nucleic acid standards may be provided only for alleles or haplotypes that are present in a population at some minimal frequency. For example, referring to the nucleic acid standards of the interfering polymorphic loci illustrated in FIG. 4A, if a first allele (empty sector (401)) at a first loci is a major allele having a frequency of 98% and a first allele (empty sector (403)) at a second loci is a major allele having a comparable frequency, then Haplotype 4 (410) may either not exist because of the lack of recombination between closely spaced loci or it may exist at an extremely low frequency. In either case, such a haplotype (or allele) may be omitted from a set of nucleic acid standards in some embodiments.

Nucleic acid standards for interfering polymorphic loci may be used together with or separately from nucleic acid standards for non-interfering polymorphic loci. Preferably, alleles of nucleic acid standards for non-interfering polymorphis loci are contained in separate DNA strands so that the ability to detect the presence or absence of heterozygosity or homozygosity at a locus may be validated, as well as the ability to generate signal in the presence of a particular allele. Likewise, for interfering polymorphic loci, preferably each haplotype of such loci is contained in a separate strand of a nucleic acid standard.

Nucleic acid standards may be used and maintained in a variety of formats. In one aspect, such standards are maintained and used as self-replicable strands or circles of DNA, such as an amplicon containing all the elements required for replication, a plasmid, or the like. Conventional cloning vectors may be used for constructing replicable nucleic acid standards. For example, suitable cloning vectors include pUC19, pNEB206A, pNEB193, and the like (available from New England Biolabs, Beverly, Mass.). Once constructed, such replicable nucleic acid standards may be maintained and propagated in conventional bacterial hosts, such as JM101, JM109, and the like. Nucleic acids having sequences corresponding to the various genetic loci of the standards may be synthesized on a commercially available automated DNA synthesizer, e.g. Applied Biosystems (Foster City, Calif.) model 3400, or like instrument, purified, combined, and inserted into a preselected site in a polylinker region of a cloning vector. After transfection and propagation in a host, the cloning vector may be recovered and its insert sequenced to confirm the identity of the nucleic acid standard.

In one aspect, nucleic acid standards may be replicated either by in vitro or in vivo techniques. Usually, nucleic acid standards are rendered capable of replication by sandwiching them between primer binding sites for in vitro amplification, e.g. using PCR, or by inserting them into a plasmid so that they may be replicated in a host cell, such as a bacterial cell. Or, a combination may be used; namely, nucleic acid standards flanked by primer binding sites may be stored and replicated in a plasmid, and they may also be replicated out of the plasmid by a PCR for use. Whether nucleic acid standards are provided in plasmids or as amplicons of linear double stranded DNA, preferably kits of the invention comprise appropriate amounts of such DNA in purified form in ready-to-use tubes, vials, ampules, or the like. Typically, such DNA may be dissolved in a TE buffer, or like solution.

The number of separate replicable nucleic acid standards employed and the number of sequences of different loci contained in each is a matter of design choice, depending on factors such as the nature of the replicable DNA, e.g. PCR amplicon, or plasmid, or the like; the convenience or expense of maintaining and handling a few versus a large number of separate replicable standards; the maximum insert size of the replicable DNA; and so on.

Figure 4A:
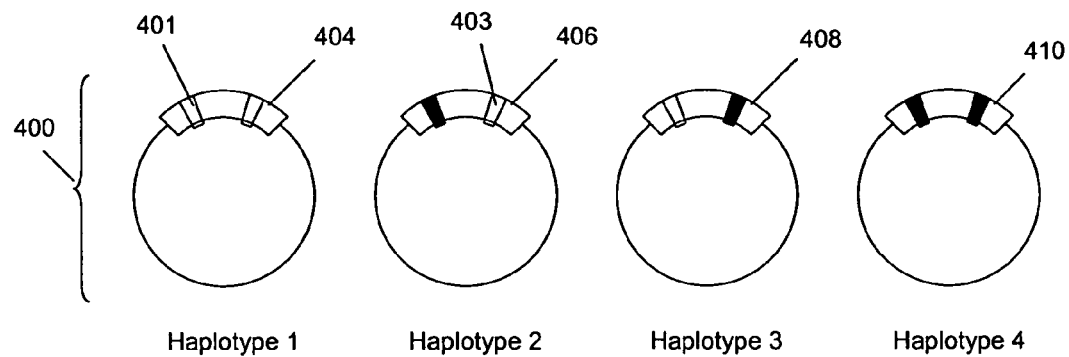
FIGS. 4A-4D illustrate aspects of nucleic acid standards of the invention.
Figure 4D:
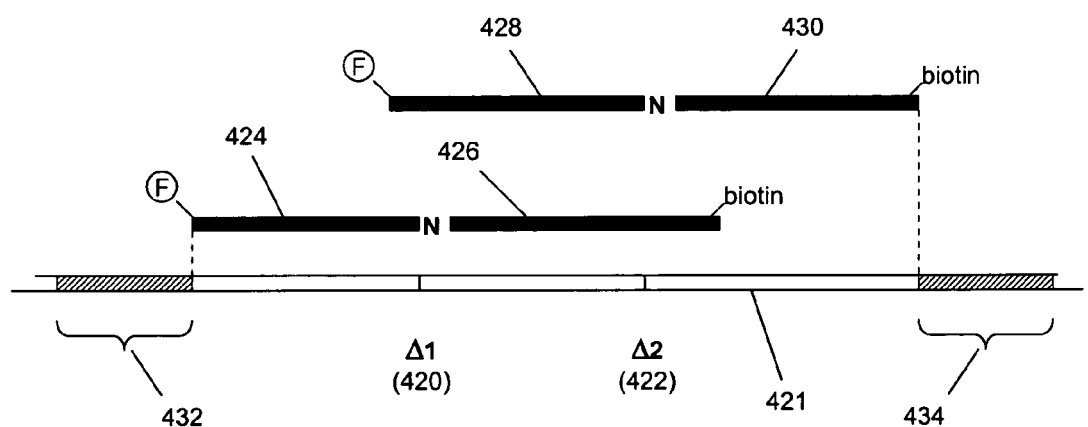
Figure 4B:
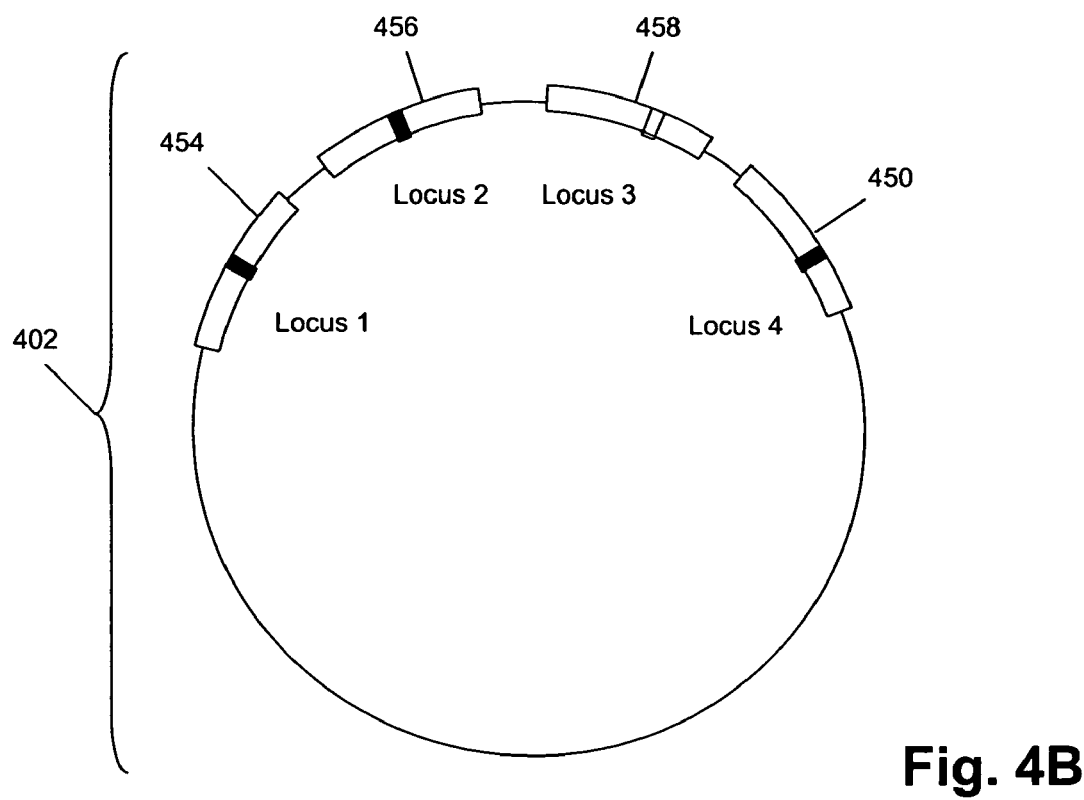
Figure 4C:
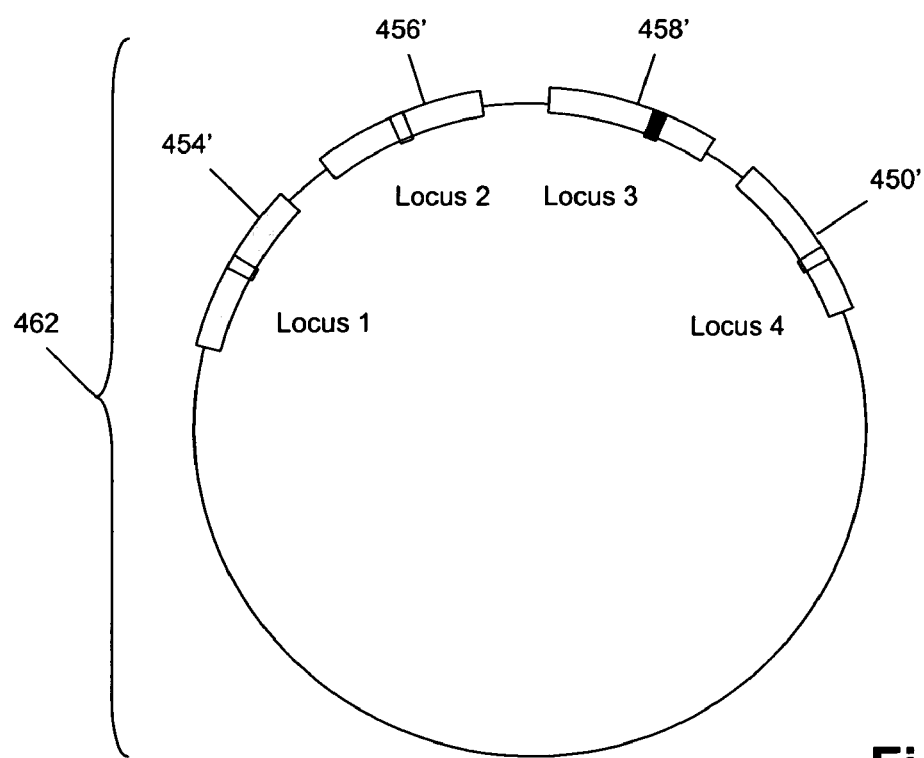

FIG. 4A illustrates nucleic acid standards for four different haplotypes of interfering polymorphic loci wherein each locus has two alleles (represented by filled and non-filled sectors). In this illustration, a set of cloning vectors (400) is provided each with different inserts (404)-(410) corresponding to the different haplotypes. Usually, the cloning vectors (400) are identical, except for their inserts. FIGS. 4B and 4C illustrates nucleic acid standards for four non-interfering loci. Each locus has two alleles (again, represented by filled and non-filled sectors) and the alleles are located in separate vectors (402) and (462).

In one aspect, when replicable nucleic acid standards are constructed, either in plasmids or other amplicons, sequences from the genome flanking each locus may be included. In one embodiment, 10 to 30 nucleotides of sequence upstream and downstream of each probe binding site are included. For interfering polymorphic loci where there are potentially overlapping probes, the flanking sequences are sequences upstream of the upstream-most probe specific for that interfering polymorphic loci and the downstream-most probe specific for that interfering polymorphic loci. In another embodiment, such flanking sequences are about 20 nucleotides in length. This feature of the invention is illustrated in FIG. 4D. Nucleic acid standard (421) for interfering polymorphic loci containing deletions (420) and (422) is shown in relation to two possible probe pairs [(424) and (426), and (428) and (430), respectively] that may hybridize to the site. In this illustration, probe (424) is the upstream-most probe and probe (430) is the downstream-most probe of the two pairs. The ends of these probes define the location of the flanking sequences (432) and (434), as indicated by the dashed lines in FIG. 4D.

The nucleic acid standards may be used in a wide range of concentrations whose selection depends on a number of factors, including the sensitivity of the hybridization-based assay employed, the amount of sample available for an assay, whether pre-assay purification or amplification steps are employed, the nature of nucleic acid extraction procedures used, and the like. In one aspect, nucleic acid standards are used at a concentration that is equivalent to the concentration of the loci being interrogated in a hybridization-based assay. In some embodiments, it may be desirable to provide concentrations of nucleic acid standards that are higher than those expected for loci in an assay mixture. For example, such higher concentrations may reduce time required to perform a test of a probe set, reduce variability due to sampling error from small reaction volumes, reduce the effects of non-specific binding to vessel walls, and like phenomena. In another aspect, nucleic acid standard concentration may be selected within the range of from about 1 femtomolar to about 10 nanomolar. In still another aspect, such concentration may be selected in the range of from about 10 femtomolar to about 1 nanomolar.

Preferably, nucleic acid standards are used in pairwise mixtures in order to represent the different zygosities of a locus being detected or measured. For example, for non-interfering polymorphic loci, a locus may have alleles "A" and "a;" thus, homozygotes AA and aa, and heterozygote Aa, would preferably each be tested separately. Likewise, for interfering polymorphic loci, each such set of loci will have a plurality of haplotypes. For example, interfering polymorphic loci containing two loci having two alleles each may have four possible haplotypes, e.g. AB, Ab, aB, and ab. Thus, a diploid individual may have any pairwise combination of such haplotypes. Typically, where one allele at each locus has a low frequency of occurrence in a population, e.g. less than 5% or less than 2%, the haplotype containing both such minor alleles, e.g. ab, is so rare in the population that a probe and/or nucleic acid standard may not be included for it, in which case the haplotypes being considered are AB, Ab, and aB. For such an embodiment, different pairwise mixtures would be produced for the following diploid configurations: Homozygotes: (AB, AB), (Ab, Ab), and (aB, aB); and Heterozygotes: (AB, Ab), (AB, aB), (Ab, aB).

Hybridization-Based Assays Employing Solid Phase Supports

Methods of conducting multiplexed hybridization-based assays using microarrays, and like platforms, suitable for the present invention are well known in the art. Guidance for selecting conditions and materials for applying labeled sequences to solid phase supports, such as microarrays, may be found in the literature, e.g. Wetmur, Crit. Rev. Biochem. Mol. Biol., 26: 227-259 (1991); DeRisi et al, Science, 278: 680-686 (1997); Chee et al, Science, 274: 610-614 (1996); Duggan et al, Nature Genetics, 21: 10-14 (1999); Schena, Editor, Microarrays: A Practical Approach (IRL Press, Washington, 2000); Freeman et al, Biotechniques, 29: 1042-

1055 (2000); and like references. Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference. Hybridization conditions typically include salt concentrations of less than about 1M, more usually less than about 500 mM and less than about 200 mM. Hybridization temperatures can be as low as 5° C., but are typically greater than 22° C., more typically greater than about 30° C., and preferably in excess of about 37° C. Hybridizations are usually performed under stringent conditions, i.e. conditions under which a probe will stably hybridize to a perfectly complementary target sequence, but will not stably hybridize to sequences that have one or more mismatches. The stringency of hybridization conditions depends on several factors, such as probe sequence, probe length, temperature, salt concentration, concentration of organic solvents, such as formamide, and the like. How such factors are selected is usually a matter of design choice to one of ordinary skill in the art for any particular embodiment. Usually, stringent conditions are selected to be about 5° C. lower than the $T_m$ for the specific sequence for particular ionic strength and pH. Exemplary hybridization conditions include salt concentration of at least 0.01 M to no more than 1 M Na ion concentration (or other salts) at a pH 7.0 to 8.3 and a temperature of at least 25° C. Additional exemplary hybridization conditions include the following: 5×SSPE (750 mM NaCl, 50 mM sodium phosphate, 5 mM EDTA, pH 7.4).

Exemplary hybridization procedures for applying labeled target sequence to a GenFlex™ microarray (Affymetrix, Santa Clara, Calif.) is as follows: denatured labeled target sequence at 95-100° C. for 10 minutes and snap cool on ice for 2-5 minutes. The microarray is pre-hybridized with 6×SSPE-T (0.9 M NaCl 60 mM $NaH_2$, $PO_4$, 6 mM EDTA (pH 7.4), 0.005% Triton X-100)+0.5 mg/ml of BSA for a few minutes, then hybridized with 120 μL hybridization solution (as described below) at 42° C. for 2 hours on a rotisserie, at 40 RPM. Hybridization Solution consists of 3M TMACL (Tetramethylammonium. Chloride), 50 mM MES ((2-[N-Morpholino]ethanesulfonic acid) Sodium Salt) (pH 6.7), 0.01% of Triton X-100, 0.1 mg/ml of Herring Sperm DNA, optionally 50 pM of fluorescein-labeled control oligonucleotide, 0.5 mg/ml of BSA (Sigma) and labeled target sequences in a total reaction volume of about 120 μL. The microarray is rinsed twice with 1×SSPE-T for about 10 seconds at room temperature, then washed with 1×SSPE-T for 15-20 minutes at 40° C. on a rotisserie, at 40 RPM. The microarray is then washed 10 times with 6×SSPE-T at 22° C. on a fluidic station (e.g. model FS400, Affymetrix, Santa Clara, Calif.). Further processing steps may be required depending on the nature of the label(s) employed, e.g. direct or indirect. Microarrays containing labeled target sequences may be scanned on a confocal scanner (such as available commercially from Affymetrix) with a resolution of 60-70 pixels per feature and filters and other settings as appropriate for the labels employed. GeneChip™ Software (Affymetrix) or like software may be used to convert the image files into digitized files for further data analysis.

Sample Preparation

Samples or specimens containing target polynucleotides may come from a wide variety of sources for use with the present invention, including cell cultures, animal or plant tissues, patient biopsies, environmental samples, or the like. Samples are prepared for assays of the invention using conventional techniques, which typically depend on the source from which a sample or specimen is taken.

Prior to carrying out reactions on a sample, it will often be desirable to perform one or more sample preparation operations upon the sample. Typically, these sample preparation operations will include such manipulations as extraction of intracellular material, e.g., nucleic acids from whole cell samples, viruses and the like. One or more of these various operations may be readily incorporated into the fluidly closed systems contemplated by the present invention.

For those embodiments where whole cells, viruses or other tissue samples are being analyzed, it will typically be necessary to extract the nucleic acids from the cells or viruses, prior to continuing with the various sample preparation operations. Accordingly, following sample collection, nucleic acids may be liberated from the collected cells, viral coat, etc., into a crude extract, followed by additional treatments to prepare the sample for subsequent operations, e.g., denaturation of contaminating (DNA binding) proteins, purification, filtration, desalting, and the like. Liberation of nucleic acids from the sample cells or viruses, and denaturation of DNA binding proteins may generally be performed by chemical, physical, or electrolytic lysis methods. For example, chemical methods generally employ lysing agents to disrupt the cells and extract the nucleic acids from the cells, followed by treatment of the extract with chaotropic salts such as guanidinium isothiocyanate or urea to denature any contaminating and potentially interfering proteins. Generally, where chemical extraction and/or denaturation methods are used, the appropriate reagents may be incorporated within a sample preparation chamber, a separate accessible chamber, or may be externally introduced.

Following extraction, it will often be desirable to separate the nucleic acids from other elements of the crude extract, e.g., denatured proteins, cell membrane particles, salts, and the like. Removal of particulate matter is generally accomplished by filtration, flocculation or the like. A variety of filter types may be readily incorporated into the device. Further, where chemical denaturing methods are used, it may be desirable to desalt the sample prior to proceeding to the next step. Desalting of the sample, and isolation of the nucleic acid may generally be carried out in a single step, e.g., by binding the nucleic acids to a solid phase and washing away the contaminating salts or performing gel filtration chromatography on the sample, passing salts through dialysis membranes, and the like. Suitable solid supports for nucleic acid binding include, e.g., diatomaceous earth, silica (i.e., glass wool), or the like. Suitable gel exclusion media, also well known in the art, may also be readily incorporated into the devices of the present invention, and is commercially available from, e.g., Pharmacia and Sigma Chemical.

In some applications, such as measuring target polynucleotides in rare cells from a patient's blood, an enrichment step may be carried out prior to conducting an assay, such as by immunomagnetic isolation. Such isolation or enrichment may be carried out using a variety of techniques and materials known in the art, as disclosed in the following representative references that are incorporated by reference: Terstappen et al, U.S. Pat. No. 6,365,362; Terstappen et al, U.S. Pat. No. 5,646,001; Rohr et al, U.S. Pat. No. 5,998,224; Kausch et al, U.S. Pat. No. 5,665,582; Kresse et al, U.S. Pat. No. 6,048,515; Kausch et al, U.S. Pat. No. 5,508,164; Miltenyi et al, U.S. Pat. No. 5,691,208; Molday, U.S. Pat. No. 4,452,773; Kronick, U.S. Pat. No. 4,375,407; Radbruch et al, chapter 23, in Methods in Cell Biology, Vol, 42

(Academic Press, New York, 1994); Uhlen et al, Advances in Biomagnetic Separation (Eaton Publishing, Natick, 1994); Safarik et al, J. Chromatography B, 722: 33-53 (1999); Miltenyi et al, Cytometry, 11: 231-238 (1990); Nakamura et al, Biotechnol. Prog., 17: 1145-1155 (2001); Moreno et al, Urology, 58: 386-392 (2001); Racila et al, Proc. Natl. Acad. Sci., 95: 4589-4594 (1998); Zigeuner et al, J. Urology, 169: 701-705 (2003); Ghossein et al, Seminars in Surgical Oncology, 20: 304-311 (2001).

In one aspect, genomic DNA for analysis is obtained using standard commercially available DNA extraction kits, e.g. PureGene® DNA Isolation Kit (Gentra Systems, Minneapolis, Minn.). In another aspect, for assaying human genomic DNA with a multiplex hybridization-based assay containing from about 1000 to 50,000 probes, a DNA sample may be used having an amount within the range of from about 200 ng to about 1 µg. When sample material is scarce, prior to assaying, sample DNA may be amplified by whole genome amplification, or like technique, to increase the total amount of DNA available for performing an assay on. Preferably, any such technique used to increase sample DNA prior to assaying does not preferentially amplify or degrade sequences so that the sequences in the sample tested are not representative of the natural genomic DNA. Several whole genome, or partial genome, amplification techniques are known in the art, such as the following which are incorporated by reference: Telenius et al, Genomics, 13: 718-725 (1992); Cheung et al, Proc. Natl. Acad. Sci., 93: 14676-14679 (1996); Dean et al, Genome Research, 11: 1095-1099 (2001); U.S. Pat. Nos. 6,124,120; 6,280,949; 6,617,137; and the like.

EXAMPLE

Genotyping Genetic Polymorphisms in Drug Metabolic Enzyme and Transporter Genes Using Circularizable Probes In this example, nucleic acid standards and molecular inversion probes (having target-specific regions of length in the range of 36 to 64 nucleotides) are prepared for 177 loci of genes in the set listed in Table I. Of these loci, interfering polymorphic loci are listed in Table II. Molecular inversion probes are designed as described in U.S. Pat. No. 6,858,412 and Hardenbol et al, Nature Biotechnology, 21: 673-678 (2003), which are incorporated herein by reference. Labeled oligonucleotide tags generated from the assay are hybridized to a GeneChip™ array of tag complements are analyzed on a GeneChip™ Scanner 3000 (Affymetrix, Santa Clara, Calif.) using the manufacturer's recommended protocols. The protocol of the above references is generally followed, subject to the following modifications, described in the MegAllele™ Genotyping System User Manual, available from the manufacturer of molecular inversion probe kits (ParAllele Bioscience, South San Francisco, Calif.). Briefly, after separation into four separate tubes, the oligonucleotide tags of successfully circularized probes ("chip tags") are amplified by PCR using primers that are labeled with one of four oligonucleotide tags ("label tag"), such that there is a unique label tag for each tube, i.e. corresponding ot A, C, G, and T, respectively. Such amplified and labeled chip tags are hybridized to a GenFlex array as described in the above references, after which haptenized oligonucleotides comprising complementary sequences of the label tags are hybridized to the array. Four different haptens (fluorescein, biotin, dinitrophenol, dansyl) are employed such that each different label tag has a different hapten attached. A mixture of four fluorescently labeled anti-hapten binding compounds are added to the array, wherein each different hapten-specific binding compound has a different fluorescent dye attached. The identity of the polymorphism detected by each probe is then resolved by detecting and characterizing the fluorescence signal generated at each hybridization site on the array, using commercially available data analysis software, e.g. ParAllele Bioscience, Inc. (South San Francisco, Calif.) or Affymetrix (Santa Clara, Calif.).

More particularly, molecular inversion probe assays are carried out in the following steps: (1) Denaturing sample and annealing probe: Four identical reactions containing 400 ng of genomic DNA for a sample, 12 amol each of 1644 probes, 0.0625 units Ampligase (Epicentre) and 0.5 units Stoffel fragment DNA polymerase (Applied Biosystems) in 9 µL of 20 mM Tris-HCl (pH 8.3), 25 mM KCl, 10 mM $MgCl_2$, 0.5 NAD and 0.01% Triton X-100 are incubated for 4 min at 20° C., 5 min at 95° C. and 15 min at 60° C. (2) Gap-fill reaction: 1 µL of each of four nucleotides is added to the four reactions and incubated for 10 min at 60° C. and then 1 min at 37° C. (3) Exonuclease selection: 10 units exonuclease I and 200 units exonuclease III (United States Biochemical) in a 2-µL volume are added and the mixture incubated for 14 min at 37° C., 2 min at 95° C. and 1 min at 37° C. (4) Uracil depurination and cleavage: 2 units of uracil-N-glycosylase (New England Biolabs) is added in 25 µL of 1.6 mM $MgCl_2$, 10 mM Tris-HCl (pH 8.3), 50 mM KCl and incubated for 9 min at 37° C. and 20 min at 95° C. (5) First amplification: 2 units of AmpliTaq Gold (Applied Biosystems), 16 pmol first primer specific for first primer binding site (302), and 16 pmol second primer specific for second primer binding site (306) in 25 µL of 1.6 mM $MgCl_2$, 10 mM Tris-HCl (pH 8.3), 50 mM KCl and 112 µm dNTP are preactivated for 10 min at 95° C. and then added to the reaction mixtures. The reactions are amplified in 28 cycles of 95° C. for 20 s, 65° C. for 45 s and 72° C. for 10 s. (6) Second amplification: For each of the four reaction mixtures, in separate PCRS, oligonucleotide tags of the molecular inversion probes are amplified and labeled with a "label tag." A separate and non-cross-hybridizing label tag is provided for each reaction mixture, i.e. one each for "A," "C," "G," and "T." Third and fourth primers anneal to third and fourth primer binding sites flanking the oligonucleotide tags ("chip tags") of the molecular inversion probes. Each third primer contains a label tag at its 5' end, and each fourth primer contains the sequence of a Dra I recognition site. (7) Tag processing: 20 units of exonuclease I and 10 units Dra I (New England Biolabs) are incubated with 60 µL of each amplification product at 37° C. for 1 h and then 80° C. for 30 min. (8) Microarray hybridization: Approximately 1.25 pmol of each amplified and processed product are hybridized overnight at 39° C. to a GenFlex Tag Array (Affymetrix) DNA array with 55 µL 2×MES, 2.2 µL 50× Denhardt buffer, 1.1 fmol (each) GenFlex control oligonucleotide (Affymetrix). (9) Wash and Staining: After washing with SSPE, or like buffer, the following are hybridized to the GenFlex array: haptenized oligonucleotides complementary to each of the label tags together with a "spacer" oligonucleotide complementary to the non-label tag portion of the third primer. After an additional wash, fluorescently labeled anti-hapten antibodies are applied to the GenFlex array followed by further washing. Data analysis is performed on the raw signal data for each array feature generated by the Affymetrix image analysis software.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

We claim:

1. A kit of nucleic acid standards for determining the presence in a probe mixture of selected probes specific for interfering polymorphic loci, the kit comprising:
   a plurality of nucleic acid standards provided in pairwise mixtures corresponding to different homozygous and heterozygous combinations of non-interfering polymorphic loci and different diploid combinations of haplotypes of interfering polymorphic loci, wherein each nucleic acid standard comprises a double stranded nucleic acid plasmid containing a nucleic acid sequence for at least one haplotype of the interfering polymorphic loci, wherein each nucleic acid standard is capable of replication and wherein there is at least one nucleic acid standard having a nucleic acid sequence complementary with each probe of the probe mixture; and
   instructions that set forth a protocol comprising the steps of: hybridizing under stringent hybridization conditions each of said pairwise mixtures of said nucleic acid standards with a mixture of probes, such that the mixture of probes comprises probes specific for at least one of said nucleic acid standards in said pairwise mixture; and detecting the presence of probes in the mixture of probes that form stable duplexes with at least one of said nucleic acid standards of said pairwise mixture to determine whether such probes are present in the mixture.

2. The kit of claim 1 wherein said nucleic acid standards contain nucleic acid sequences of said interfering polymorphic loci in genes selected from HLA genes, tumor suppressor genes, cell cycle control genes, oncogenes, or genes encoding xenobiotic metabolizing enzymes.

3. The kit of claim 2 wherein said interfering polymorphic loci are in genes encoding said xenobiotic metabolizing enzymes that are selected from the group consisting of ABCB1, ABCC2, CYP1A2, CYP2A6, CYP2B6, CYP2C19, CYP2C8, CYP2C9, CYP2D6, CYP3A4, CYP3A5, DPYD, FMO3, GSTM1, NAT 1, NAT2, SLC21A6, SLC22A1, SLC22A2, TPMT, and UGT1A1.

4. The kit of claim 2 wherein said interfering polymorphic loci are in genes encoding said xenobiotic metabolizing enzymes that are selected from the group consisting of CYP1A1, CYP1B1, CYP2C18, CYP3A7, GSTT1, GSTM3, GSTA1, UGT1A6, UGT1A7, UGT2B4, UGT2B7, UGT2B15, ADH1B, ALDH2, APE1, CDKN2A, COMT, DRD2, DRD4, EPHX1, ERCC1, ERCC2, ERCC4, ERCC5, GRPR, GSTA4, LIG3, MDM2, MGMT, MPG, NQO1, OGG1, PCNA, POLB, SLC6A3, SOD2, TP53, XRCC1, XRCC2, XRCC3, XRCC9, ABCB1, CYP2E1, GSTP1, SLC22A2, ABCC2, CYP2J2, NAT1, TPMT, CDA, CYP3A4, NAT2, UGT1A1, CYP1A2, CYP3A5, CYP2C8, CYP2A6, DPYD, CYP2C9, CYP2B6, FMO2, SLC15A2, CYP2C19, FMO3, SLC21A6, CYP2D6, GSTM1, and SLC22A1.

* * * * *